United States Patent [19]

Treuner et al.

[11] 3,956,290
[45] May 11, 1976

[54] [(THIOPHOSPHONOTHIO)ACETAMIDO]-CEPHALOSPORIN DERIVATIVES

[75] Inventors: Uwe D. Treuner; Hermann Breuer, both of Regensburg, Germany

[73] Assignee: E. R. Squibb & Sons, Inc., Princeton, N.J.

[22] Filed: Jan. 20, 1975

[21] Appl. No.: 542,329

Related U.S. Application Data

[62] Division of Ser. No. 258,687, June 1, 1972, Pat. No. 3,914,221.

[52] U.S. Cl. .............................. 260/243 C; 260/941; 260/999
[51] Int. Cl.² ...................................... C07D 501/28
[58] Field of Search ............................... 260/243 C

[56] References Cited
UNITED STATES PATENTS

| | | | |
|---|---|---|---|
| 3,870,713 | 3/1975 | Hamanaka | 260/243 C |
| 3,880,845 | 4/1975 | Treuner | 260/243 C |

*Primary Examiner*—Raymond V. Rush
*Attorney, Agent, or Firm*—Lawrence S. Levinson; Merle J. Smith

[57] ABSTRACT

[(Thiophosphono)acetamido]cephalosporin derivatives of the general formula

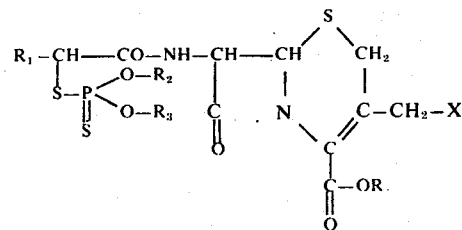

wherein R is hydrogen, lower alkyl, aralkyl, tri(lower alkyl)silyl, tri(lower alkyl)stannyl, a salt forming ion or the group

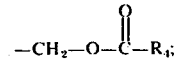

$R_1$ is hydrogen; $R_2$, $R_3$ and $R_4$ each is lower alkyl, or aralkyl; and X is hydrogen, hydroxy or lower alkanoyloxy; are useful as antibacterial agents.

8 Claims, No Drawings

[(THIOPHOSPHONOTHIO)ACETAMIDO]CEPHALOSPORIN DERIVATIVES

This application is a division of application Ser. No. 258,687, filed June 1, 1972, Pat. No. 3,914,221, Oct. 21, 1975.

SUMMARY OF THE INVENTION

This invention relates to new [(thiophosphonothio)acetamido]cephalosporin derivatives of the formula

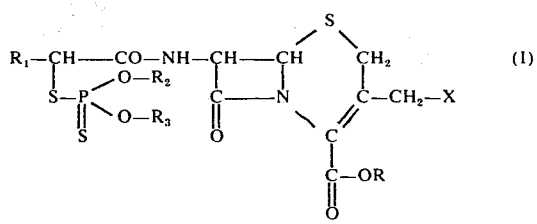

R represents hydrogen, lower alkyl, aralkyl, tri(lower alkyl)silyl, tri(lower alkyl)stannyl, a salt forming ion or the group

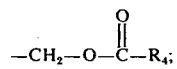

$R_1$ represents hydrogen, lower alkyl, aryl, aralkyl or certain heterocyclic groups; $R_2$ and $R_3$, which are preferably the same, each represents lower alkyl, aryl or aralkyl or $R_2$ and $R_3$ may join together to form a 2 or 3 carbon polymethylene bridge completing a 5- or 6-membered ring with oxygen and phosphorus; $R_4$ represents lower alkyl, aryl or aralkyl. X is hydrogen, hydroxy, lower alkanoyloxy, aroyloxy, aralkanoyloxy, $SR_2$,

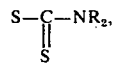

$OR_2$, the radical of a nitrogen base, a quaternary ammonium radical, or together X and R represent a bond linking carbon and oxygen in a lactone ring.

The preferred members within each group are as follows: R is hydrogen, lower alkyl, alkali metal, trimethylsilyl or

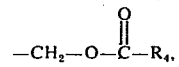

especially hydrogen, methyl, pivaloyloxy, sodium or potassium; $R_1$ is phenyl, thienyl, furyl or pyridyl, especially phenyl, $R_2$ and $R_3$ each is lower alkyl, especially methyl or ethyl; $R_4$ is lower alkyl, preferably methyl or t-butyl; and X is preferably hydrogen or acetoxy.

DETAILED DESCRIPTION OF THE INVENTION

The various groups represented by the symbols have the meanings defined below and these definitions are retained throughout this specification.

The lower alkyl groups are straight or branched chain hydrocarbon radicals having one to eight carbons in the chain, for example, methyl, ethyl, propyl, isopropyl, butyl, isobutyl, n-butyl, t-butyl, amyl or the like.

The aryl groups are monocyclic carbocyclic aryl groups including simply substituted members. By way of illustration, this includes the phenyl ring and simply substituted phenyl containing one to three substituents $R_5$ (preferably only one), such as the halogens (chlorine and bromine being preferred), lower alkyl groups such as those defined above, lower alkoxy groups, (i.e., lower alkyl of the type defined above attached to an oxygen), hydroxy, carboxy and the like. In the case of the last two named substituents there is preferably only one, especially in the para position of the phenyl. Illustrative are phenyl, o-, m- and p-chlorophenyl, o-, m- and p-bromophenyl, 3,4-dichlorophenyl, 3,5-dibromophenyl, o-, m- and p-tolyl, p-methoxyphenyl, 3,4,5-trimethoxyphenyl, p-hydroxyphenyl, p-carboxyphenyl and the like.

The aralkyl groups include a monocyclic carbocyclic aryl group attached to a lower alkyl group, both as defined above. Illustrative are benzyl, o-, m- or p-chlorobenzyl, o-, m- or p-bromobenzyl, o-, m- or p-methylbenzyl, phenethyl, p-chlorophenethyl, 3,5-diethylbenzyl, 3,4,5-trichlorobenzyl and the like.

The lower alkanoyloxy, aroyloxy and aralkanoyloxy groups represented by X include the acyl group of acid esters. The lower alkanoyl radicals are the acyl radicals of lower fatty acids containing alkyl radicals of the type described above. The lower alkanoyloxy groups include, for example, acetoxy, propionyloxy, butyryloxy and the like. The aroyloxy groups are derived from monocyclic carbocyclic aryl groups of the kind described. Similarly the aralkanoyloxy groups consist of monocyclic carbocyclic aryl and alkanoyloxy radicals of the type described. The sulfur containing substituents represented by X bear the same type of groups. X also represents the radical of an amine, e.g., an alkylamine like methylamine, ethylamine, dimethylamine, triethylamine, aralkylamine like dibenzylamine, pyridinium, 1-quinolinium, 1-picolinium, etc. X and R may also join together, as indicated above, to form a bond linking carbon and oxygen in a lactone ring.

The heterocyclic groups represented by $R_1$ are thienyl, furyl, pyridyl and isothiazolyl radicals as well as these heterocyclics with one or two substituents $R_6$ including halo, lower alkyl (particularly methyl and ethyl), lower alkoxy (particularly methoxy and ethoxy) or phenyl.

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, dibenzylamine, N,N-dibenzylethylenediamine, methylamine, triethylamine, procaine, N-ethylpiperidine, etc. The ester forming tri(lower alkyl)silyl and tri(lower alkyl)stannyl groups include, for example, trimethylsilyl, triethylsilyl, tri-n-butyl stannyl and the like. $R_2$ and $R_3$ in addition to representing the individual substituents indicated may together be two or three methylene groups, (e.g., derived from ethylene glycol or propylene glycol) joining in a bridge which forms a 5- or 6-membered ring with the two oxygen atoms and the phosphorus.

The new [(thiophosphonothio)acetamido]cephalosporin derivatives of this invention are produced by reacting a 7-aminocephalosporanic acid compound of formula II [which includes 7-aminocephalosporanic acid (7-ACA), 7-amino-3-desacetoxycephalosporanic acid (7-ADCA) and other derivatives], or an activated derivative, of the formula

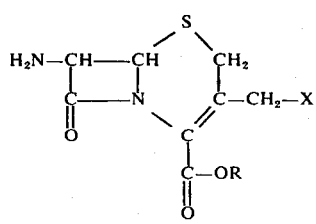

with a dithiophosphoric acid ester of the formula

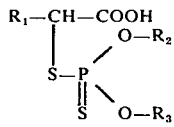

The dithiophosphoric acid esters of formula III are produced by the reaction of a compound of formula IV with a compound of formula V

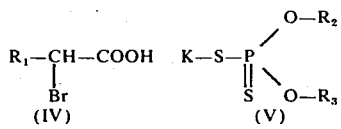

[The compounds of formula V are produced by the method described in Houben-Weyl,Methoden der Organischen Chemie, Vol. XII/2, pages 684–686 (1964)]. The halogen in the acid IV may be chlorine instead of bromine and the sodium as well a potassium salt of V may be used.

The activated derivatives referred to include, for example, the reaction product with an anhydride forming reagent such as ethylchloroformate, benzoyl chloride, pivaloyl chloride, etc., or with bis-imidazolecarbonyl, dicyclohexylcarbodiimide, p-nitrophenol or the like.

The reaction between the 7-aminocephalosporanic acid compound and the dithiophosphoric acid ester may be effected, for example, by dissolving or suspending the latter in an inert organic solvent such as chloroform, methylenechloride, dioxane, benzene or the like, and adding, at about room temperature or below, about an equimolar amount of an anhydride forming reagent, e.g., ethyl chloroformate, benzoylchloride or the like, or other activating compound such as dicyclohexylcarbodiimide, along with a salt forming organic base, such as triethylamine, pyridine or the like, followed, after an interval, by the addition of the 7-aminocephalosporanic acid compound. The product of the reaction is then isolated by conventional procedures, e.g., by concentration or evaporation of the solvent.

When R is the acyloxymethyl group

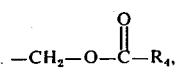

this group may be introduced into the 7-aminocephalosporanic acid moiety prior to the reaction with the dithiophosphoric acid ester or the activated derivative by treatment with 1 to 2 moles of a halomethyl ester of the formula hal—CH$_2$OCOR$_4$      VI wherein hal is halogen, preferably chlorine or bromine, in an inert organic solvent such as dimethylformamide, acetone, dioxane, benzene or the like, at about ambient temperature or below.

As an alternative, a product of formula I may be produced by reacting a compound of the formula

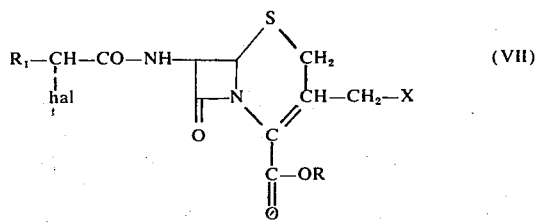

or a derivative thereof with a compound of the formula

in the presence of a tertiary alkylamine like triethylamine, or with a salt of VIII, e.g., a metal salt such as an alkali metal salt, in a solvent such as dimethylformamide. Hal is halogen, preferably chlorine or bromine and R and R$_1$ are the same as above. The metal salts are obtained by reacting a dithiophosphoric acid ester with the appropriate metal in a lower alkanol or with the metal alkoxide, e.g., potassium ethoxide.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 200 mg./kg., daily, orally or parenterally, in single or two to four divided doses to treat infections of bacterial origin, e.g., 5.0 mg./kg. in mice.

Oral forms give prompt high blood levels which are maintained for relatively long periods.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.01 to 1% by weight of such compounds admixed with, suspended or dissolved in conventional inert dry or aqueous carriers for application by washing or spraying. They are also useful as nutritional supplements in animal feeds.

The following examples are illustrative of the invention. All temperatures are on the centigrade scale. Additional variations may be produced in the same manner by appropriate substitution in the starting material.

EXAMPLE 1

7-[2-[(Diethoxythiophosphono)thio]acetamido]cephalosporanic acid and potassium salt 2 g. (5 mM) of 7-bromoacetamidocephalosporanic acid are dissolved in absolute dimethylformamide and a solution of 1.12 g. (5mM) of potassium dithiophosphoric acid O,O diethyl ester is added. A precipitate of potassium bromide forms immediately. After stirring for ten minutes, the reaction mixture is poured into 250 ml. of ice water and extracted three times with 100 ml. portions of ethyl acetate. The ethyl acetate extracts are combined, shaken with 2 × 50 ml. portions of water, then dried over sodium sulfate and concentrated. There are obtained 1.5 g. of light yellow crystals of 7-[2-[(diethoxythiophosphono)thio]acetamido]cephalosporanic acid, m.p. 80° (dec.); potassium salt m.p. 115° (dec.).

EXAMPLE 2

7-[2-[(Diethoxythiophosphono)thio]-2-phenylacetamido]cephalosporanic acid

By substituting 5mM of 7-(2-bromo-2-phenylacetamido-cephalosporanic acid for the 7-bromoacetamidocephalosporanic acid in the procedure of Example 1, there are obtained 2.1 g. of yellow crystalline 7-[2-[(diethoxythiophosphono)thio]-2-phenylacetamido]cephalosporanic acid, m.p. 45° (dec.).

EXAMPLE 3

7-[2-[(Dimethoxythiophosphono)thio]acetamido]-cephalosporanic acid

By substituting 5mM of potassium dithiophosphoric acid dimethyl ester for the diethyl ester in the procedure of Example 1, 1.2 g. of 7-[2-[(dimethoxythiophosphono)thio]acetamido]-cephalosporanic acid are obtained as a viscous oil.

EXAMPLE 4

7-[2-[(Diethoxythiophosphono)thio]acetamido]-3-desacetoxy-cephalosporanic acid

By substituting 5mM of 7-bromo-3-desacetoxycephalosporanic acid for the 7-bromoacetamidocephalosporanic acid in the procedure of Example 1, there is obtained 7-[2-[(diethoxythiophosphono)thio]acetamido]-3-desacetoxycephalosporanic acid, m.p. 48°–50°.

The following additional products having the formula in the right hand side of the table are obtained by the procedure of Example 1 from the potassium dithiophosphoric acid ester in the left hand part of the table and the 7-bromoacetamidocephalosporanic acid having the indicated R and X substituents.

TABLE

| Example | $R_2$ | $R_3$ | R | $R_1$ | $R_2$ | $R_3$ | X |
|---|---|---|---|---|---|---|---|
| 5 | $CH_3$ | $CH_3$ | $CH_3$ | H | $CH_3$ | $CH_3$ | H |
| 6 | $C_2H_5$ | $C_2H_5$ | K | $CH_3$ | $C_2H_5$ | $C_2H_5$ | OH |
| 7 | $C_2H_5$ | $C_2H_5$ | K | $C_3H_7$ | $C_2H_5$ | $C_2H_5$ | pyridinium |
| 8 | $C_6H_5CH_2$ | $C_6H_5CH_2$ | $-CH_2OC(=O)-CH(CH_3)_2$ | $C_6H_5CH_2$ | $C_6H_5CH_2$ | $C_6H_5CH_2$ | $OCOCH_3$ |
| 9 | $C_6H_5CH_2$ | $C_6H_5CH_2$ | $-CH_2OC(=O)-C_6H_5$ | $C_6H_5$ | $C_6H_5$ | $C_6H_5CH_2$ | $OCOCH_3$ |
| 10 | $C_2H_5$ | $C_2H_5$ | H | $3,4-(CH_3O)_2C_6H_3$ | $C_2H_5$ | $C_2H_5$ | H |
| 11 | $C_2H_5$ | $C_2H_5$ | K | $3,4,5-(CH_3O)_3C_6H_2$ | $C_2H_5$ | $C_2H_5$ | $OCOCH_3$ |
| 12 | $C_6H_5$ | $C_6H_5$ | Na | $4-CH_3C_6H_4$ | $C_6H_5$ | $C_6H_5$ | $OCOCH_3$ |
| 13 | $C_6H_5CH_2$ | $C_6H_5CH_2$ | lactone (+X) | $3,4-(Br)_2C_6H_3CH_2$ | $C_6H_5CH_2$ | $C_6H_5CH_2$ | lactone (+R) |
| 14 | $C_2H_5$ | $C_2H_5$ | H | $2,4-(Cl)_2C_6H_3$ | $C_2H_5$ | $C_2H_5$ | $OCOCH_3$ |
| 15 | $CH_3$ | $CH_3$ | Na | (thienyl) | $CH_3$ | $CH_3$ | H |
| 16 | $C_6H_5CH_2$ | $C_6H_5CH_2$ | $C_6H_5CH_2$ | (furyl) | $C_6H_5CH_2$ | $C_6H_5CH_2$ | $OOCH_2C_6H_5$ |
| 17 | $C_6H_5$ | $C_6H_5$ | $CH_2OC(=O)-C(CH_3)_3$ | $C_6H_5$ | $C_6H_5$ | $C_6H_5$ | H |
| 18 | $CH_3$ | $CH_3$ | $CH_2O-C(=O)-C(CH_3)_3$ | $C_6H_5$ | $CH_3$ | $CH_3$ | $OOC-C_6H_5$ |

TABLE-continued

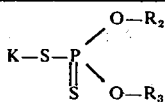
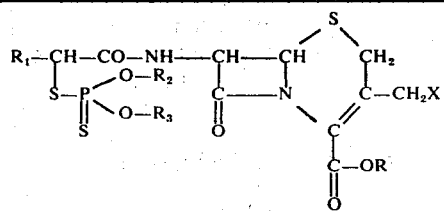

| Example | $R_2$ | $R_3$ | R | $R_1$ | $R_2$ | $R_3$ | X |
|---|---|---|---|---|---|---|---|
| 19 | $C_2H_5$ | $C_2H_5$ | $CH_2O-\overset{O}{\underset{\|}{C}}-C(CH_3)_3$ | $C_6H_5$ | $C_2H_5$ | $C_2H_5$ | $OCOCH_3$ |
| 20 | $C_2H_5$ | $C_2H_5$ | K | 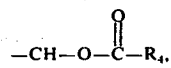 | $C_2H_5$ | $C_2H_5$ | $OCOCH_3$ |
| 21 | $C_2H_5$ | $C_2H_5$ | K | $C_6H_5$ | $C_2H_5$ | $C_2H_5$ | $SCH_3$ |
| 22 | $C_2H_5$ | $C_2H_5$ | K | $C_6H_5$ | $C_2H_5$ | $C_2H_5$ | $S-\overset{H}{\underset{\overset{\|}{S}}{C}}-N-CH_3$ |
| 23 | $-CH_2CH_2-$ | | K | $C_6H_5$ | $-CH_2CH_2-$ | | H |
| 24 | $C_2H_5$ | $C_2H_5$ | K | $C_6H_5$ | $C_2H_5$ | $C_2H_5$ | $OCH_3$ |
| 25 | $C_2H_5$ | $C_2H_5$ | $Si(CH_3)_3$ | $C_6H_5$ | $C_2H_5$ | $C_2H_5$ | H |
| 26 | $C_2H_5$ | $C_2H_5$ | $Sn(n\text{-butyl})_3$ | $C_6H_5$ | $C_2H_5$ | $C_2H_5$ | H |

What is claimed is:

1. A compound of the formula

wherein R is hydrogen, lower alkyl, phenyl-lower alkyl, tri(lower alkyl)silyl, tri(lower alkyl)stannyl,

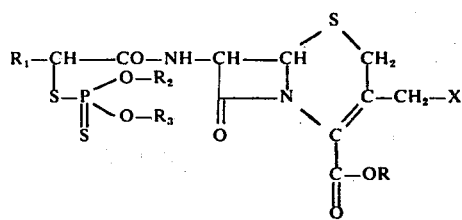

aluminum, alkali metal, alkaline earth metal or tri(lower alkyl)amine; $R_1$ is hydrogen; $R_2$, $R_3$ and $R_4$ each is lower alkyl or phenyl-lower alkyl; and X is hydrogen, hydroxy or lower alkanoyloxy, said lower alkyl and lower alkanoyloxy groups having up to eight carbon atoms.

2. A compound as in claim 1 wherein $R_2$ and $R_3$ each is lower alkyl.

3. A compound as in claim 1 wherein R and X each is hydrogen, $R_2$ and $R_3$ each is lower alkyl.

4. A compound as in claim 1 wherein R is hydrogen, $R_2$ and $R_3$ each is lower alkyl and X is lower alkanoyloxy.

5. A compound as in claim 1 wherein R and $R_1$ each is hydrogen, $R_2$ and $R_3$ each is lower alkyl and X is acetoxy.

6. A compound as in claim 5 wherein each alkyl group is ethyl.

7. A compound as in claim 5 wherein each alkyl group is methyl.

8. A compound as in claim 3 wherein each alkyl group is ethyl.

* * * * *